United States Patent [19]
Moenning et al.

[11] Patent Number: 6,039,725
[45] Date of Patent: Mar. 21, 2000

[54] APPARATUS AND METHOD FOR SECURING A MEDICAL INSTRUMENT TO A CANNULA OF A TROCAR ASSEMBLY

[76] Inventors: Stephen P. Moenning, 124 Hibiscus, Punta Gorda, Fla. 33950; Charles Manker, 35 N. Greenbay Rd., Lake Forest, Ill. 60045

[21] Appl. No.: 09/185,335

[22] Filed: Nov. 3, 1998

Related U.S. Application Data

[62] Division of application No. 08/840,668, Apr. 29, 1997.

[51] Int. Cl.⁷ .................................................. A61M 25/00
[52] U.S. Cl. ............................. 606/1; 606/108; 606/185; 604/108
[58] Field of Search ................................ 606/1, 108, 130, 606/185; 604/174, 164, 246, 264, 108, 247, 116, 283

[56] References Cited

U.S. PATENT DOCUMENTS

| | | |
|---|---|---|
| 3,762,404 | 10/1973 | Sakita . |
| 4,809,694 | 3/1989 | Ferrara . |
| 4,874,378 | 10/1989 | Hillstead ................................ 604/167 |
| 4,969,870 | 11/1990 | Kramer et al. ............................. 604/51 |
| 5,016,644 | 5/1991 | Guirguis . |
| 5,042,502 | 8/1991 | Guirguis . |
| 5,073,169 | 12/1991 | Raiken . |
| 5,176,648 | 1/1993 | Holmes et al. . |
| 5,201,742 | 4/1993 | Hasson . |
| 5,215,531 | 6/1993 | Maxson et al. . |
| 5,217,451 | 6/1993 | Freitas ........................................ 606/1 |
| 5,354,283 | 10/1994 | Bark et al. . |
| 5,364,367 | 11/1994 | Banks et al. . |
| 5,375,588 | 12/1994 | Yoon . |
| 5,405,330 | 4/1995 | Zunitch et al. .......................... 604/240 |
| 5,476,460 | 12/1995 | Montalvo . |
| 5,478,318 | 12/1995 | Yoon . |
| 5,540,648 | 7/1996 | Yoon . |
| 5,562,728 | 10/1996 | Lazarus et al. ............................. 623/1 |
| 5,564,439 | 10/1996 | Picha . |
| 5,651,771 | 7/1997 | Tangherlini et al. . |
| 5,658,272 | 8/1997 | Hasson ........................................ 606/1 |
| 5,865,817 | 2/1999 | Moenning et al. ..................... 604/283 |

FOREIGN PATENT DOCUMENTS

| | | |
|---|---|---|
| 0 648 470 A1 | 4/1995 | European Pat. Off. . |
| WO 94/25095 | 11/1994 | WIPO . |
| WO 95/11050 | 4/1995 | WIPO . |

OTHER PUBLICATIONS

Invitation to Pay Additional Fees with Annex to Form PCT/ISA/206. Communication Relating to the Results of the Partial International Search dated Jul. 3, 1998.

International Search Report dated Sep. 17, 1998.

*Primary Examiner*—Linda C. M. Dvorak
*Assistant Examiner*—Sonya Harris-Ogugua
*Attorney, Agent, or Firm*—Maginot, Addison & Moore

[57] ABSTRACT

An apparatus for securing a medical instrument to a cannula of a trocar assembly includes a first retainer portion. The apparatus also includes a second retainer portion. The apparatus also includes a ball-shaped instrument holder. The ball-shaped instrument holder has a passageway extending therethrough. The instrument is securable within the passageway. A method for securing a medical instrument to a cannula of a trocar assembly is also disclosed.

8 Claims, 13 Drawing Sheets

APPARATUS AND METHOD FOR SECURING A MEDICAL INSTRUMENT TO A CANNULA OF A TROCAR ASSEMBLY

This application is a divisional of co-pending application Ser. No. 08/840,668, filed on Apr. 29, 1997.

CROSS REFERENCE

Cross reference is made to copending U.S. patent application Ser. No. 08/840,669, entitled "Apparatus and Method for Securing a Cannula of a Trocar Assembly to a Body of a Patient" by Stephen P. Moenning and Charles Manker, which was filed on Apr. 29, 1997.

BACKGROUND OF THE INVENTION

The present invention relates generally to a trocar assembly, and more specifically to an apparatus and method for securing a medical instrument to a cannula of a trocar assembly.

Minimally invasive surgical techniques, such as laparoscopic surgery, typically include the use of a trocar assembly to create a small hole or port in a wall of a body cavity in order to gain access to the body cavity. More specifically, the trocar assembly typically includes a plastic tube or cannula in which a trocar is received. The trocar has a sharp, three-cornered tip at one end thereof and is used to pierce the wall of the body cavity in order to permit the insertion of the trocar assembly into the body cavity. Thereafter, the trocar is withdrawn or otherwise removed from the cannula thereby permitting the ingress of medical instruments, such as a laparoscope, into the body cavity via the cannula.

Surgery performed by using these minimally invasive techniques is generally results in lower postoperative morbidity, shorter postoperative stay, less postoperative pain, decreased cost, and quicker recovery as compared to "open" or conventional surgical techniques. Because of the aforementioned advantages, these minimally invasive techniques are being applied to an increasing variety of surgical procedures. For example, laparoscopic procedures for the resection of malignancies have emerged. In particular, laparoscopic colectomy for carcinoma of the colon has been developed, and it has been reported in various surgical publications that the initial results of these procedures have advantages over operations performed in the traditional open manner. Moreover, it is hoped that the long term results of these procedures will be comparable, or better than, those performed in the traditional open manner.

However, the use of such minimally invasive surgical techniques creates a number of challenges for a surgeon. For example, after the cannula and thereafter the medical instrument have been inserted into the body cavity, the cannula, along with the medical instrument therein, must be physically supported. More specifically, mechanical support must be exerted onto the cannula in order to stabilize or otherwise prevent the movement of the cannula and hence the medical instrument therein.

In addition, it is desirable to selectively permit the cannula and/or the medical instrument therein to be rotated or tilted. In particular, during some minimally invasive surgical techniques it may be advantageous to permit the surgeon to rotate or tilt the cannula and/or the instrument therein in order to provide enhanced manipulation within the body cavity.

The cannula and/or the medical instrument therein are often manually held in place. In particular, after the surgeon has inserted and correctly positioned the cannula and the medical instrument within the body cavity, a nurse or other member of a surgical team, physically holds the cannula and the medical instrument in place in order to stabilize the cannula and the medical instrument throughout the duration of the surgery. If during the surgery the surgeon desires to rotate or tilt the cannula and/or the medical instrument therein, the surgeon reclaims support of the cannula and the medical instrument from the nurse, repositions the cannula and/or the medical instrument, and returns support of the cannula and the medical instrument to the nurse. It should be appreciated that a plurality of trocar assemblies and hence cannulae and medical instruments may be used during a given surgery. Therefore, costs associated with the surgery may be increased due to the need to have one or more nurses present during the surgery in order to support the plurality of cannulae and medical instruments being used.

Alternatively, a number of devices have heretofore been designed which are fastened at a first end to a surgical table or bed, and at a second end to the cannula of the trocar assembly and the medical instrument thereby supporting the same. However, such devices are generally bulky, expensive, and often obstruct the surgeon's access to the patient.

Moreover, there is a rapid addition of new technologies into the field of minimally invasive surgery such as remote access minimally invasive surgery and robotic minimally invasive surgery. Such technologies may be facilitated by a device that is (1) portable, (2) capable of repeatably positioning the cannula and the medical instrument in a number of predetermined positions, and (3) capable of stabilizing the cannula and the medical instrument once the same are positioned in one of a number of predetermined positions.

What is needed therefore is an apparatus for securing a medical instrument to a cannula of a trocar assembly. What is also needed is an apparatus for securing a medical instrument to a cannula of a trocar assembly which allows the angle and position of the cannula relative to the body to be easily and quickly altered. What is further needed is an apparatus for securing a medical instrument to a cannula of a trocar assembly which is inexpensive. What is moreover needed is an apparatus for securing a medical instrument to a cannula of a trocar assembly which does not obstruct the surgeon's access to the patient. What is yet further needed is an apparatus for securing a medical instrument to a cannula of a trocar assembly which is portable. What is also needed is an apparatus for securing a medical instrument to a cannula of a trocar assembly which is capable of repeatably positioning the cannula and the medical instrument in a number of predetermined positions. What is also needed is an apparatus for securing a medical instrument to a cannula of a trocar assembly which is capable of stabilizing the cannula and the medical instrument once the same are positioned in one of a number of predetermined positions. In addition, what is needed is an apparatus for securing a medical instrument to a cannula of a trocar assembly which is reusable, but may also be disposed after each use.

SUMMARY OF THE INVENTION

In accordance with a first embodiment of the present invention, there is provided an apparatus for securing a medical instrument to a cannula of a trocar assembly. The apparatus includes a retainer body. The apparatus also includes an instrument holder securable to the retainer body. The instrument holder has a passageway extending therethrough. The instrument is positionable within the passageway.

In accordance with a second embodiment of the present invention, there is provided a method for securing a medical instrument to a cannula of a trocar assembly. The method includes the step of attaching an instrument retainer to the cannula. The instrument retainer includes an instrument holder. The instrument holder has a passageway extending therethrough. The method also includes the step of inserting the instrument through the passageway.

In accordance with a third embodiment of the present invention, there is provided an apparatus for securing a medical instrument to a cannula of a trocar assembly. The apparatus includes a first retainer portion. The apparatus also includes a second retainer portion. The apparatus also includes a ball-shaped instrument holder. The ball-shaped instrument holder has a passageway extending therethrough. The instrument is securable within the passageway.

It is therefore an object of the present invention to provide a new and useful apparatus for securing a medical instrument to a cannula of a trocar assembly.

It is a further object of the present invention to provide an improved apparatus for securing a medical instrument to a cannula of a trocar assembly.

It is moreover an object of the present invention to provide a new and useful method for securing a medical instrument to a cannula of a trocar assembly.

It is yet another object of the present invention to provide an improved method for securing a medical instrument to a cannula of a trocar assembly.

It is a further object of the present invention to provide an apparatus for securing a medical instrument to a cannula of a trocar assembly which allows the angle and position of the instrument relative to the cannula to be easily and quickly altered.

It is yet another object of the present invention to provide an apparatus for securing a medical instrument to a cannula of a trocar assembly which is inexpensive.

It is moreover an object of the present invention to provide an apparatus for securing a medical instrument to a cannula of a trocar assembly which does not obstruct the surgeon's access to the patient.

It is another object of the present invention to provide an apparatus for securing a medical instrument to a cannula of a trocar assembly which is portable.

It is also an object of the present invention to provide an apparatus for securing a medical instrument to a cannula of a trocar assembly which is capable of repeatably positioning the cannula and the medical instrument in a number of predetermined positions.

It is moreover an object of the present invention to provide an apparatus for securing a medical instrument to a cannula of a trocar assembly which is capable of stabilizing the cannula and the medical instrument once the same are positioned in one of a number of predetermined positions.

It is yet a further object of the present invention to provide an apparatus for securing a medical instrument to a cannula of a trocar assembly which is reusable, but may also be disposed after each use.

The above and other objects, features, and advantages of the present invention will become apparent from the following description and the attached drawings.

DETAILED DESCRIPTION OF THE INVENTION

Figure 1:
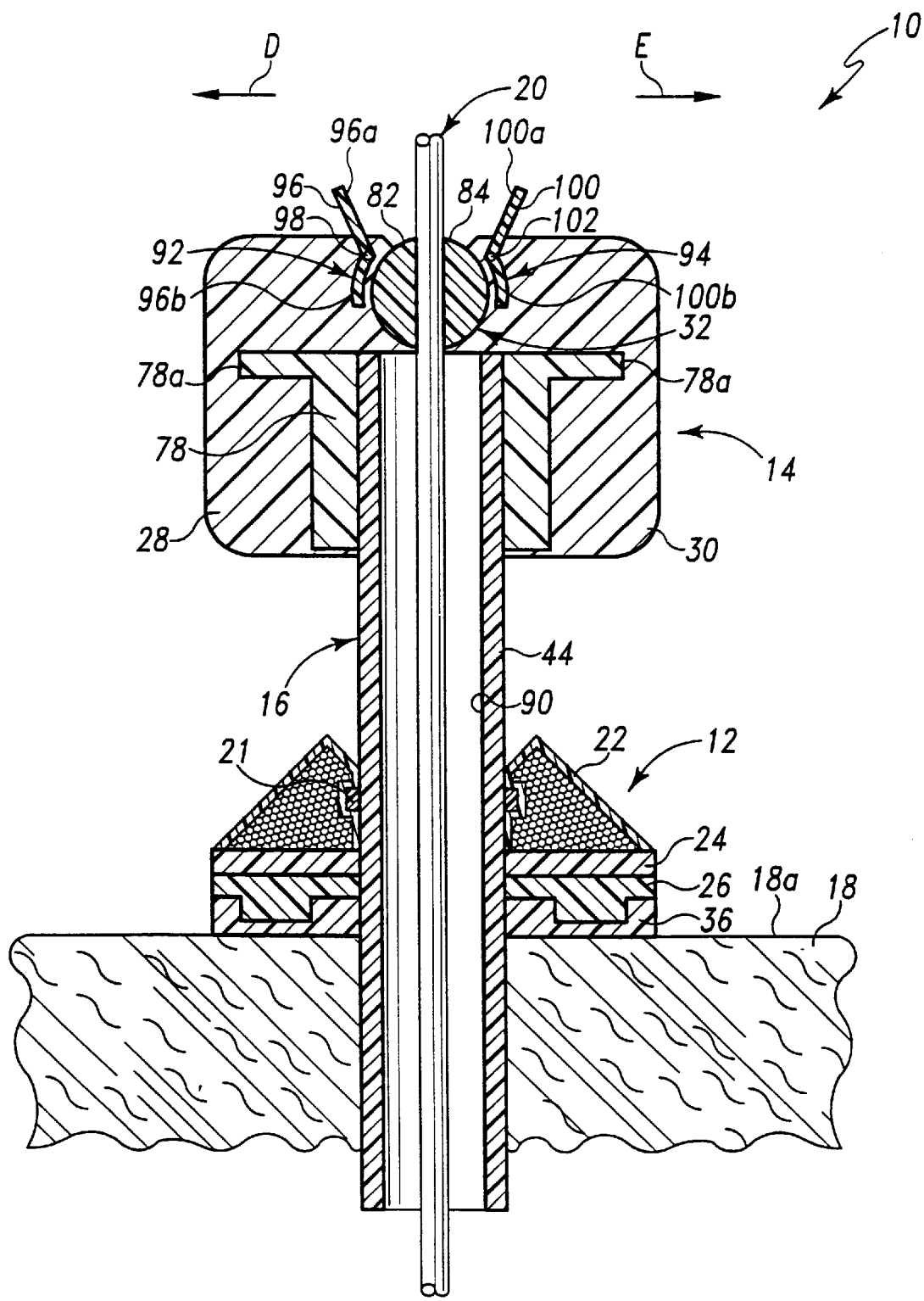
FIG. 1 is a cross sectional view of a cannula and instrument retaining assembly which incorporates the features of the present invention therein (Note: the medical instrument 20 is not shown in cross-section for clarity of description)

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Referring now to FIG. 1 there is shown a cannula and instrument retaining assembly 10. The cannula and instrument retaining assembly includes a cannula retainer 12 and an instrument retainer 14. The cannula retainer 12 secures a cannula 16 of a trocar assembly to a portion of a body 18. The instrument retainer 14 secures a medical instrument 20, such as a laparoscope or grasper, to the cannula 16.

The cannula retainer 12 includes an enclosed structure 22, a base 24, a slider 26, and a locator 36. The enclosed structure 22 is adhesively or otherwise non-movably affixed to the base 24. The base 24 is rotatably secured to the slider 26. The slider 26 is slidably secured to the locator 36.

Figure 2:
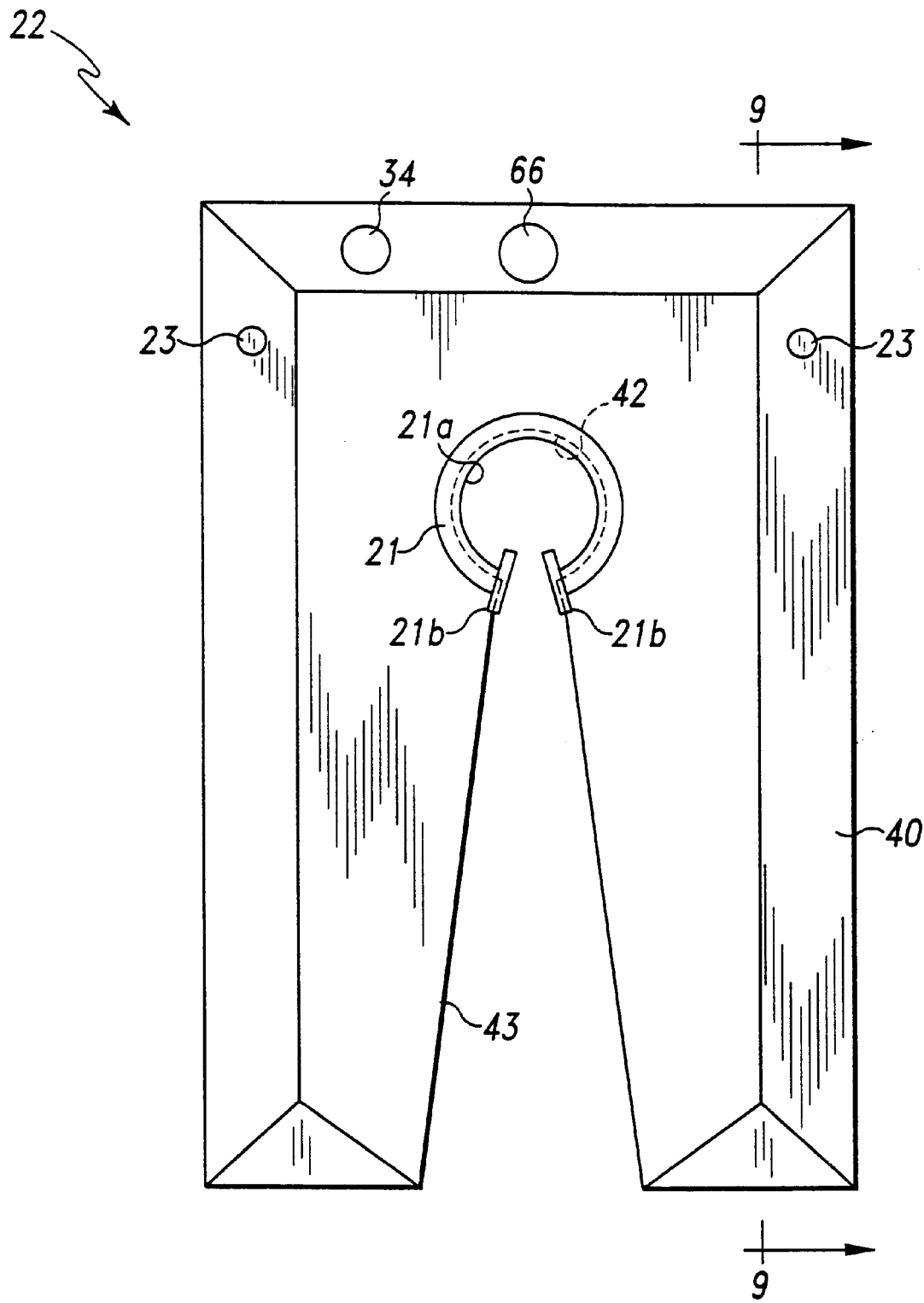
FIG. 2 is an enlarged top elevational view of the enclosed structure of the cannula and instrument retaining assembly of FIG. 1.

The enclosed structure 22 includes a rectangular-shaped fluid impervious bag 40 having a cylindrically-shaped access opening 42 defined therein (see also FIG. 2). One flexible fluid-impervious bag which may be used in the present invention with some modifications is described in U.S. Pat. No. 3,762,404 issued to Sakita, the disclosure of which is herein incorporated by reference.

Figure 8:
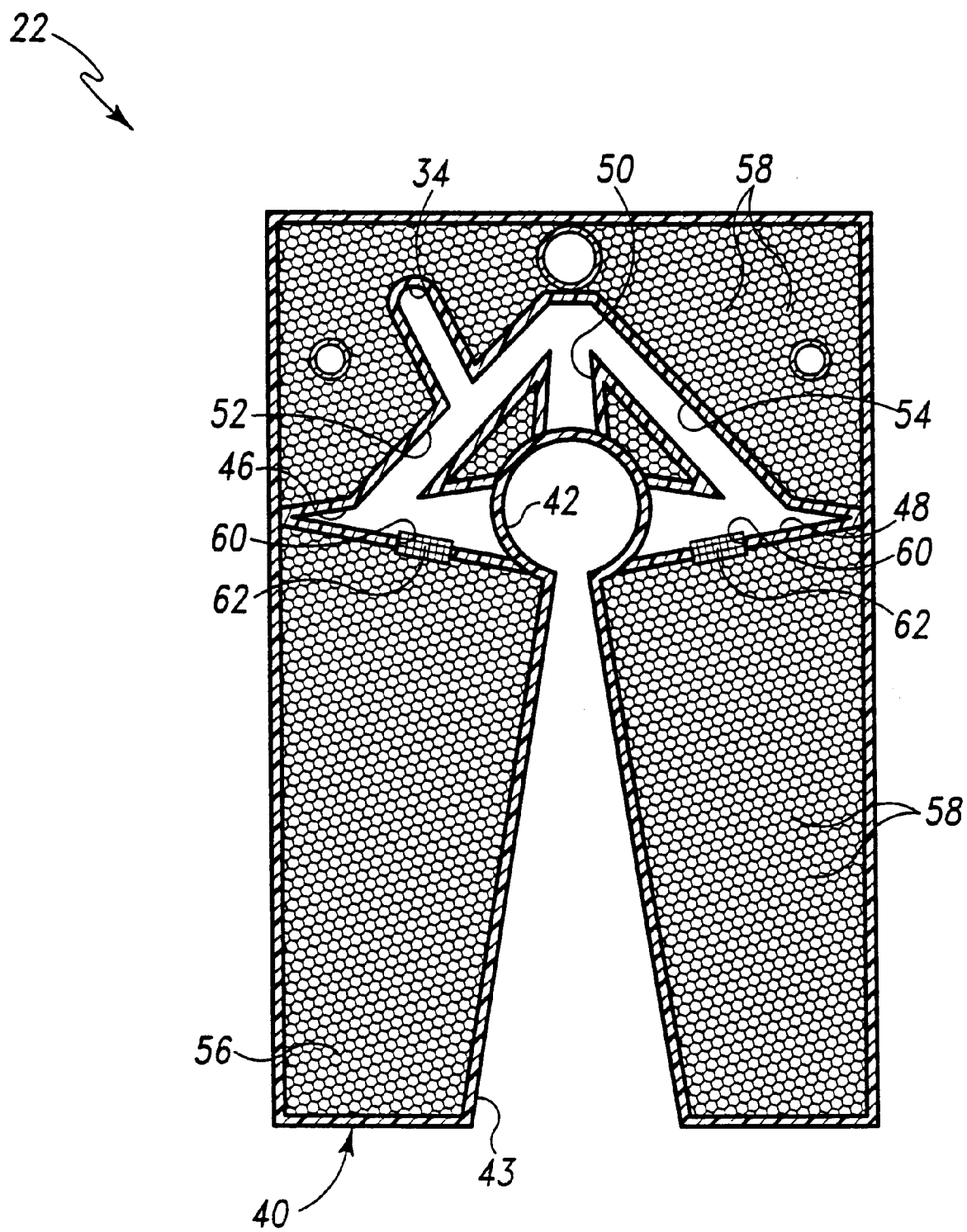
FIG. 8 is a cross sectional view of the enclosed structure taken along the line 8—8 of FIG. 3, as viewed in the direction of the arrows (Note: the cannula retaining ring 21 and the ring supports 19 have been removed for clarity of description)

The enclosed structure 22 includes a fluid port 34 as shown in FIG. 2. Moreover, the enclosed structure 22 includes a number of collapsible fluid chambers 46, 48, and 50 as shown in FIG. 8. The collapsible fluid chambers 46, 48, and 50 are in fluid communication with the fluid port 34. In particular, the collapsible fluid chambers 46 and 50 are coupled to one another as well as the fluid port 34 via a fluid passageway 52 as shown in FIG. 8. The collapsible fluid chamber 48 is coupled to the collapsible fluid chamber 50 via a fluid passageway 54. Hence, the collapsible fluid chamber 48 is in fluid communication with the fluid port 34 via a fluid path which includes the fluid passageway 54, the collapsible fluid chamber 50, and the fluid passageway 52.

Figure 3:
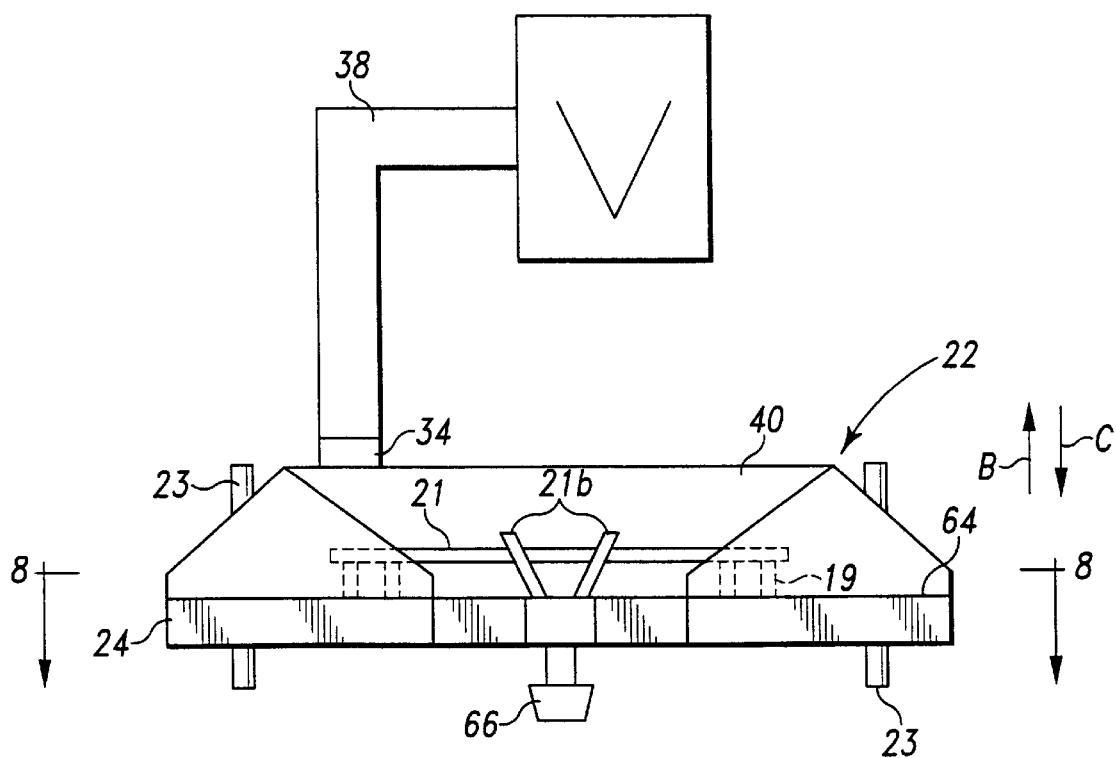
FIG. 3 is an enlarged front elevational view of the enclosed structure and the base of the cannula and instrument retaining assembly of FIG. 1, with the enclosed structure being shown schematically coupled to the vacuum source V.

The fluid port 34 is in fluid communication with a vacuum source V as shown in FIG. 3. More specifically, the fluid port 34 includes a fluid valve (not shown) which is coupled to the vacuum source V via a vacuum line 38. The fluid valve may be any of a number of well known valves capable of maintaining and then releasing a vacuum. For example, the fluid valve may be a trumpet valve or a conventional two- or three-way stop cock valve. The fluid port 34 may be used to increase the fluid pressure within the bag 40. In particular, the fluid valve may be selectively used to release a vacuum from within the bag 40 thereby placing the bag 40 in an ambient mode of operation.

The vacuum source V is used to evacuate the bag 40 and thereby place the bag 40 in an evacuated mode of operation. The vacuum source V may be manually operated or power driven. Examples of vacuum sources V which may be used in the present invention include a wall suction apparatus, an aspirator pump, or any other conveniently operating vacuum source V.

The bag 40 further includes a bead chamber 56 as shown in FIG. 8. The bead chamber 56 contains a plurality of beads 58 therein. The beads 58 must be sufficiently rigid to withstand the stresses that result when they interengage upon evacuation of the bead chamber 56. The beads 58 must also have a high mechanical strength so that the bead chamber 56 can be repeatedly evacuated without the accompanying attrition or fracture of the beads 58. The beads 58 should also be elastically deformable such that when the bead chamber 56 is evacuated they can freely move into close interengagement with one another to form a stable, rigid structure.

The beads 58 are preferably made of an expanded plastic material which has high mechanical strength, elastic deformability and low specific gravity. Examples of such plastic materials include polystyrene and polyvinyl chloride. The term "specific gravity" is intended to mean a true specific gravity. Thus, when such beads are configured in order to be hollow, the specific gravity of the beads 58 is represented by the weight of the beads 58 divided by the total volume of the beads 58 including the hollow space therein. The specific gravity of the beads 58 used in the present invention is preferably in the range of from about 0.1 to about 0.6. Such values are readily attainable with foamed synthetic resins. However, it should be appreciated that other materials may be used for the beads 58 provided such materials have a low specific gravity in the range specified above and satisfy the mechanical strength and elastic deformability requirements.

The beads 58 used in the present invention may be from about 1 to about 5 millimeters in diameter. Moreover, the beads 58 are preferably uniform in size and shape. However, a mixture of substantial portions of beads of at least two materially different sizes within the indicated range may also be used. In addition, the beads 58 may vary in shape. For example, the beads 58 may be configured as cubes, as opposed to spheres, and may also be electrostatically charged thereby increasing the affinity between adjacent beads 58 when the bag 40 is placed in its evacuated mode of operation.

The bead chamber 56 is in fluid communication with the fluid port 34. In particular, the collapsible fluid chambers 46 and 48 each includes a number of ports 60 in fluid communication with the bead chamber 56. Each of the ports 60 includes a screen 62. The screens 62 have an appropriate mesh size to prevent the entrance of the beads 58 into the collapsible fluid chambers 46 and 48. It should be appreciated that the diameter of the ports 60 may be configured to allow the passage of air therethrough, while preventing the passage of the beads 58 into the collapsible fluid chambers 46 and 48 thereby eliminating the need for the screens 62.

When a first end of the vacuum line 38 (see FIG. 3) is attached to the fluid port 34 via the fluid valve (not shown), and a second end of the vacuum line 38 is attached to the vacuum source V (see FIG. 3) and thereafter a vacuum is created by the vacuum source V, the ports 60 allow the passage of a fluid, such as air, from the bead chamber 56 into the collapsible fluid chambers 46 and 48 while preventing the beads 58 from entering the collapsible fluid chambers 46 and 48.

Air which is present in the bead chamber 56 when the bag 40 is placed in its ambient mode of operation allows the beads 58 to move freely relative one another thereby giving the bag 40 a pliable, deformable structure. However, when the bag 40 is placed in its evacuated mode of operation in which air within the bead chamber 56 is evacuated via the vacuum source V, the beads 58 are interengaged with one another thereby preventing relative movement therebetween. This causes the bag 40 to possess a stable, rigid structure.

A portion 44 (see FIG. 1) of the cannula 16 is received into the access opening 42 of the enclosed structure 22. When air is present in the bead chamber 56 (i.e. either the fluid port 34 is not in fluid communication with the vacuum source V or the fluid valve associated with the fluid port 34 is positioned to allow the ingress of air into the enclosed structure), the cannula 16 is movable relative the enclosed structure 22 thereby allowing a surgeon to position the cannula 16 in a number of different angles and positions relative the body 18. However, once the surgeon has positioned the cannula 16 in a desired angle and position, air is excavated from the bag 40. In particular, the fluid port 34 is placed in fluid communication with the vacuum source V and the fluid valve associated with the fluid port 34 is positioned to prevent the ingress of air into the enclosed structure thereby evacuating air from the bead chamber 56.

Figure 9:
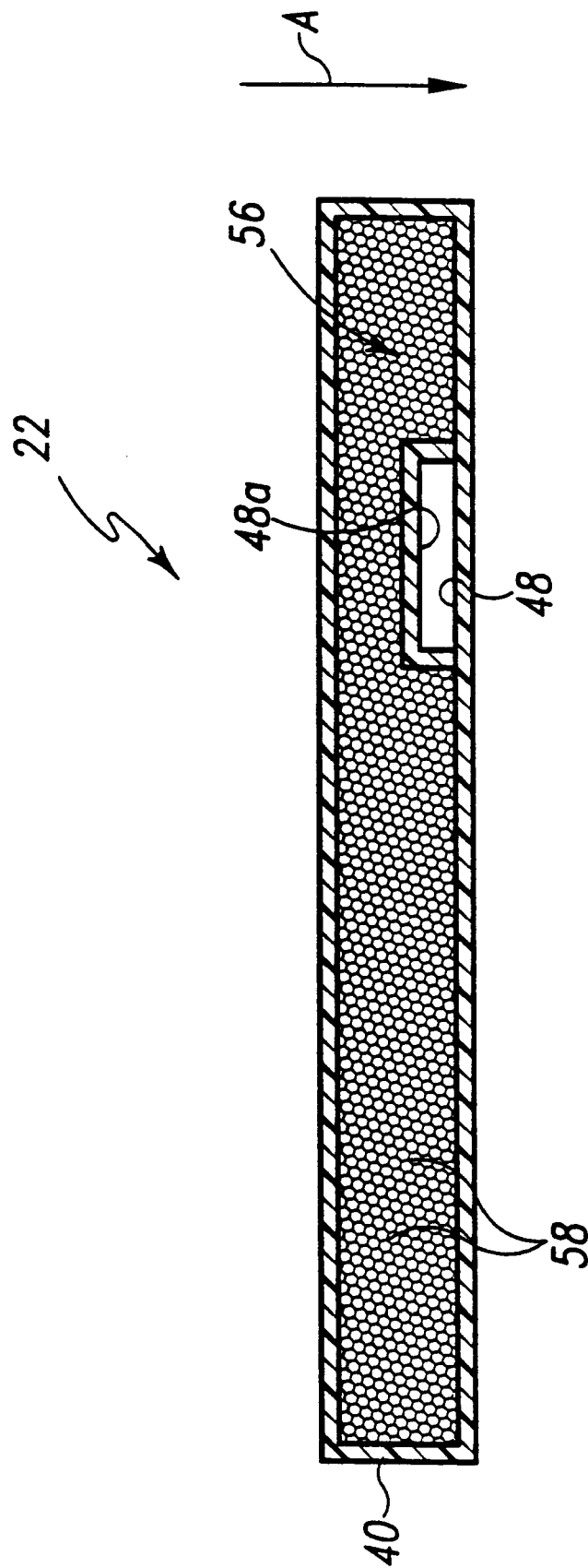
FIG. 9 is a cross sectional view of the enclosed structure taken along the line 9—9 of FIG. 2, as viewed in the direction of the arrows (Note: the cannula retaining ring 21 and the ring supports 19 have been removed for clarity of description)

Placing the bag 40 in its evacuated mode of operation in which the bead chamber 56 is in fluid communication with the vacuum V causes the collapsible fluid chambers 46, 48, and 50 to collapse thereby decreasing the diameter of the access opening 42. In particular, as the collapsible fluid chambers 46, 48, and 50 collapse, the beads 58 displace the volume which was previously occupied by the air within the collapsible fluid chambers 46, 48, and 50. For example, as air is evacuated from the collapsible fluid chamber 48, a top surface 48a thereof is urged in the general direction of arrow A of FIG. 9. Thereafter, the beads 58 adjacent the top surface 48a occupy the volume previously occupied by the air within the collapsible fluid chamber 48.

By reducing the diameter of the access opening 42 in the manner described above when the bag 40 is placed in its evacuated mode of operation, the cannula 16 is secured to the enclosed structure 22. In particular, the size of the collapsible fluid chambers 46, 48, and 50 are predetermined in order to cause the diameter of the access opening 42 to be reduced to a predetermined size upon the evacuation of air therefrom in order to prevent the portion 44 of the cannula 16 from moving relative to the access opening 42.

The enclosed structure 22 has an elongated channel 43 defined therein as shown in FIG. 2. An open end of the elongated channel 43 is provided to receive the cannula 16 therein. More specifically, if the cannula 16 is already positioned in the body 18 prior to the attachment of the cannula retainer 12, the open end of the channel 43 allows the cannula 16 to be received through the elongated channel 43 and into the access opening 42 without requiring the surgeon to remove the cannula 16 from the body 18.

A bottom surface 64 (see FIG. 3) of the enclosed structure 22 is adhesively or otherwise affixed to the base 24 thereby non-movably securing the bag 40 and hence the enclosed structure 22 to the base 24. Moreover, the base 24 has an attaching plug 66 extending therefrom as shown in FIG. 3. The attaching plug 66 is received into an attaching aperture 67 defined in the slider 26 (see FIG. 4) thereby rotatably securing the base 24 to the slider 26. For example, the attaching plug 66 may be snap-fit into the attaching aperture 67.

A cannula retaining ring 21 is secured to the base 24 via a number of ring supports 19 as shown in FIG. 3. The cannula retaining ring 21 defines an opening 21a (see FIG. 2) in which the cannula 16 is secured. The cannula retaining ring 21 supports the cannula 16 thereby preventing the cannula 16 from moving upwardly or downwardly. However, if it is desirable to move the cannula 16 upwardly or downwardly, the surgeon may squeeze a pair of tabs 21b defined in the cannula retaining ring 21 thereby allowing the cannula 16 to be moved upwardly and downwardly relative to the cannula retaining ring 21. It should be appreciated that the cannula retaining ring 21 may be made of a deformable, elastomeric material such as rubber.

The base 24 has a number of locking pins 23 movably secured thereto. In particular, the locking pins 23 may be moved in the general directions of arrows B and C of FIG. 3 thereby allowing the locking pins 23 to be advanced into and out of a number of locking holes 25 defined in the slider 26 (see FIG. 4).

Figure 4:
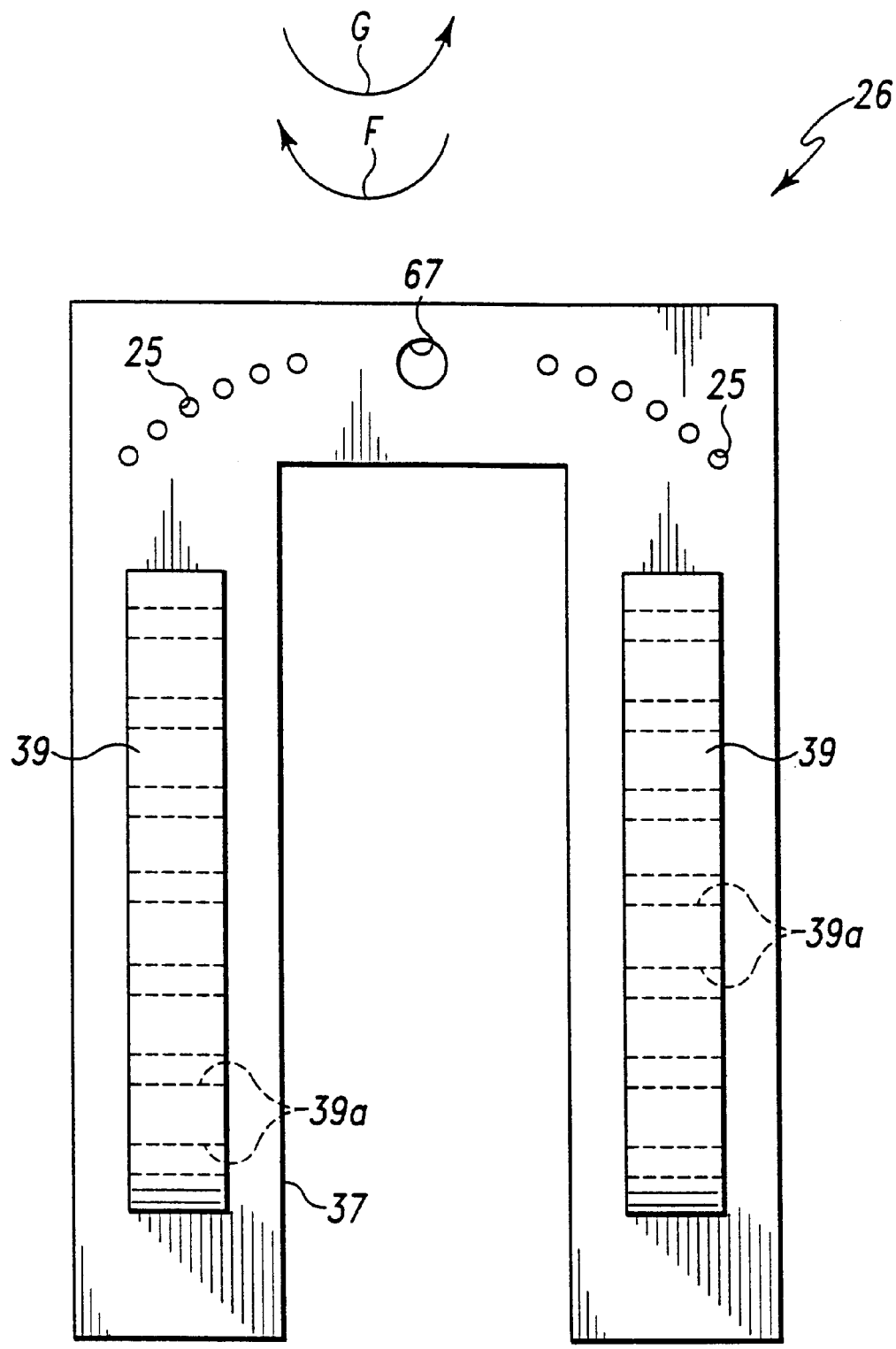
FIG. 4 is an enlarged top elevational view of the slider of the cannula and instrument retaining assembly of FIG. 1.
Figure 5:
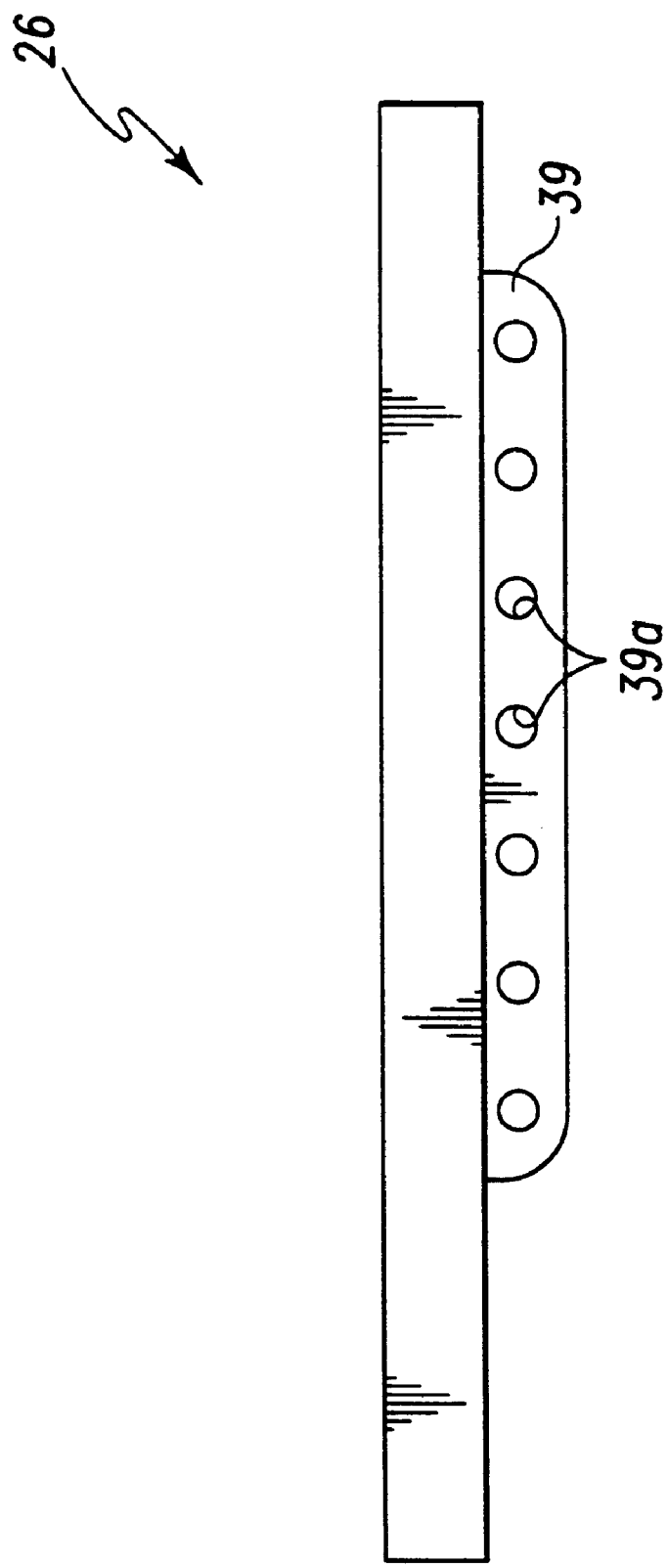
FIG. 5 is a side elevational view of the slider of FIG. 4.

Referring now to FIGS. 4–5, there is shown the slider 26. The slider 26 has a channel 37 defined therein. An open end of the channel 37 is provided to receive the cannula 16 therein. More specifically, if the cannula 16 is already positioned in the body 18 prior to the attachment of the cannula retainer 12, the open end of the channel 37 allows the cannula 16 to be positioned within the channel 35 without requiring the surgeon to remove the cannula 16 from the body 18.

The locking holes 25 are defined in the slider 26 in a configuration which allows the base 24 to be rotated relative to the slider 26 and thereafter locked thereto. In particular, the base 24 may be rotated in the general directions of arrows F and G of FIG. 4 and thereafter locked to the slider 26 by advancing one or both of the locking pins 23 into one or both of the locking holes 25.

The slider 26 has a pair of tongues 39 extending therefrom as shown in FIG. 5. The tongues 39 have a number of locating apertures 39a defined therein. As shall be discussed in more detail below, the tongues 39 cooperate with a pair of grooves 72 defined in the locator 36 in order to slidably secure the slider 26 to the locator 36.

Figure 6:
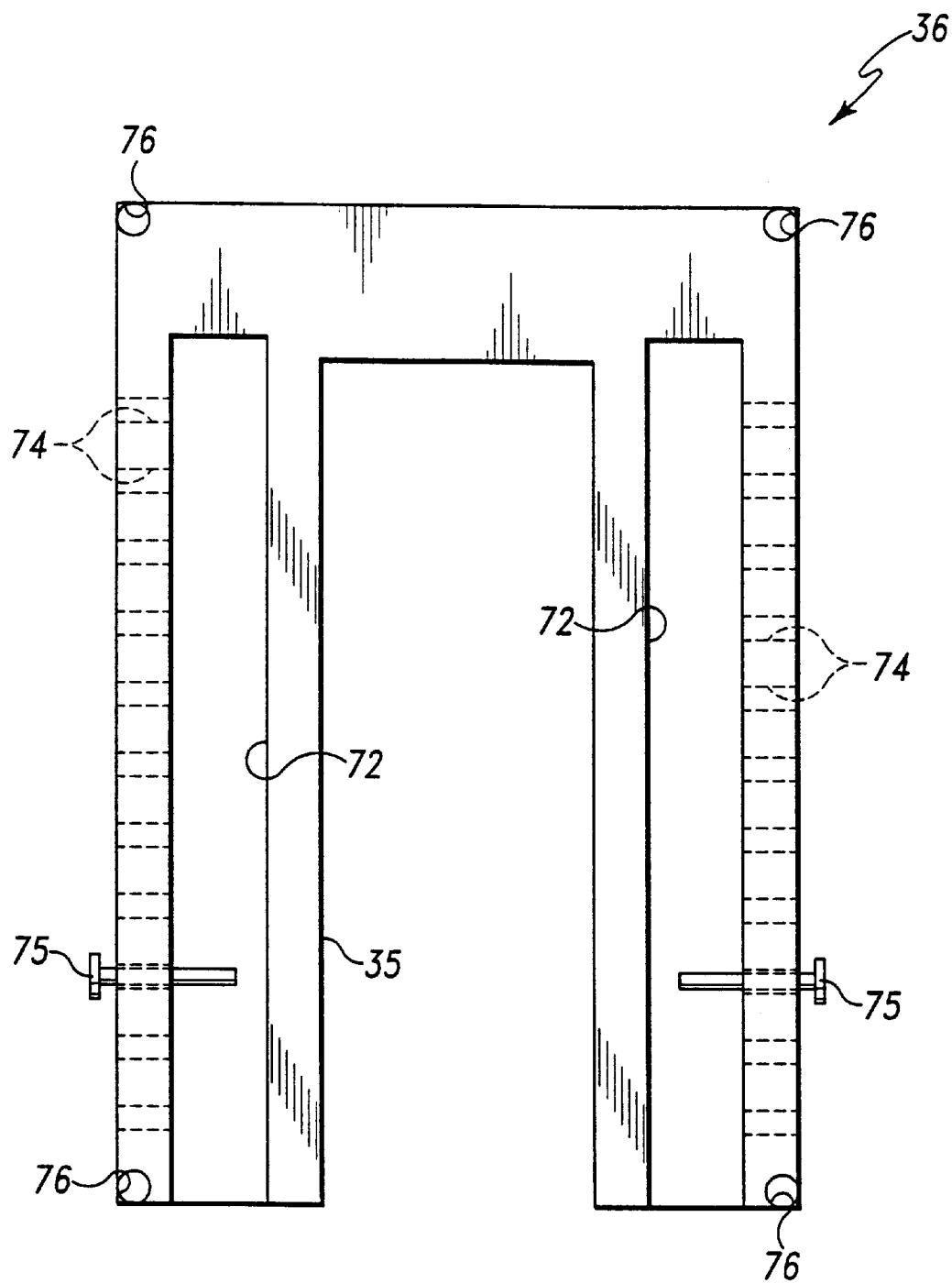
FIG. 6 is an enlarged top elevational view of the locator of the cannula and instrument retaining assembly of FIG. 1.
Figure 7:
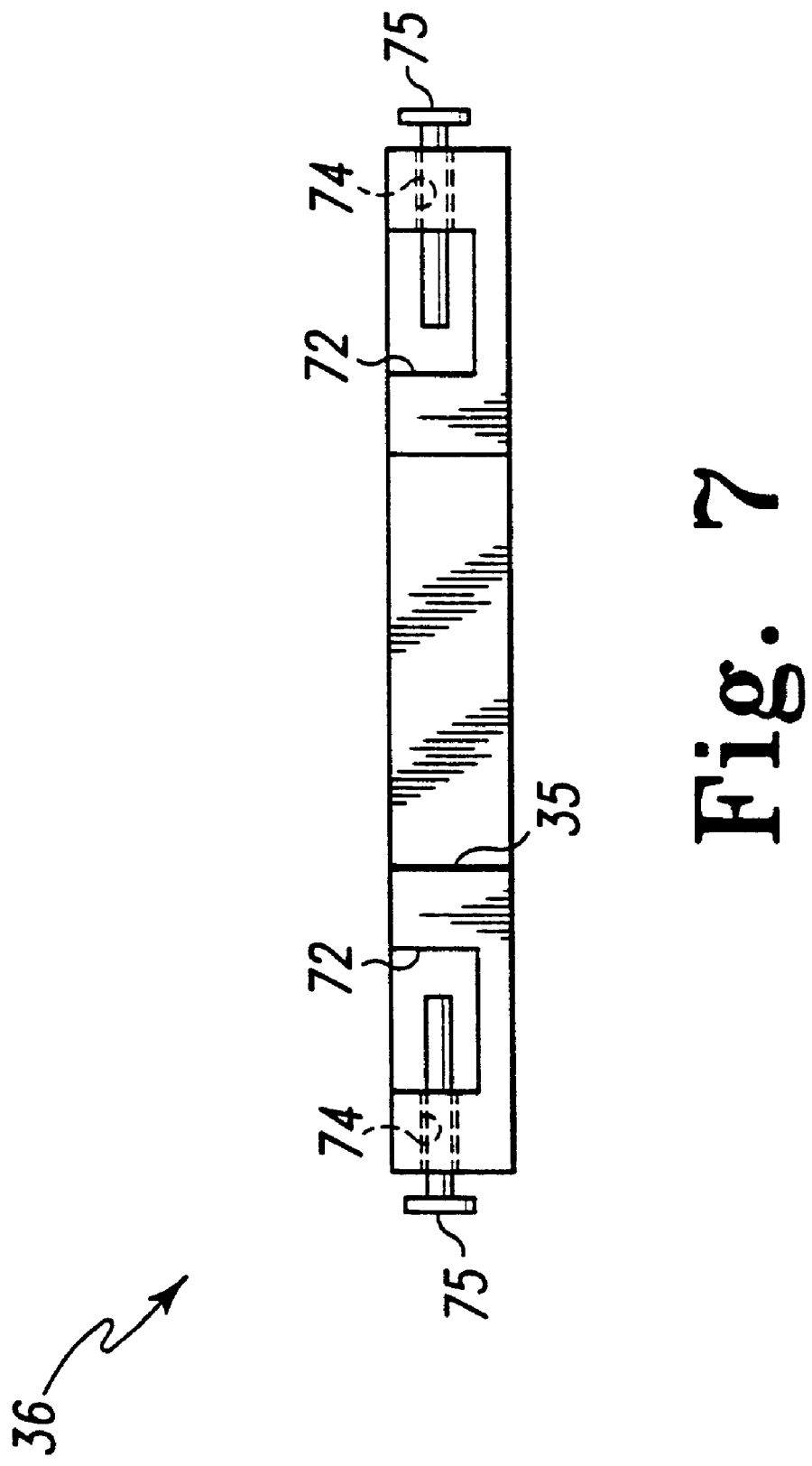
FIG. 7 is an front elevational view of the locator of FIG. 6.

Referring now to FIGS. 6–7, there is shown the locator 36. The locator 36 has a channel 35 defined therein. An open end of the channel 35 is provided to receive the cannula 16 therein. More specifically, if the cannula 16 is already positioned in the body 18 prior to the attachment of the cannula retainer 12, the open end of the channel 35 allows the cannula 16 to be positioned within the channel 35 without requiring the surgeon to remove the cannula 16 from the body 18.

The locator 36 has a number of suture holes 76 defined therein as shown in FIG. 6. The suture holes 76 may be used to suture the locator 36 to an outer surface 18a of the body 18 (see FIG. 1) thereby non-movably securing the locator 36 to the outer surface 18a of the body 18. It should be appreciated that the locator 36 may be secured to the outer surface 18a of the body 18 in any other acceptable manner which prevents the locator 36 from moving relative to the outer surface 18a of the body 18. For example, the locator 36 may be adhesively affixed to the outer surface 18a of the body 18.

As discussed above, the tongues 39 of the slider 26 (see FIG. 4) are received into the grooves 72 thereby slidably securing the slider 26 and hence the base 24 to the locator 36. The locator 36 has a number of positioning holes 74 defined therein as shown in FIG. 6. The positioning holes 74 receive a number of pins 75 therein in order to secure the slider 26 to the locator 36. In particular, one of the locating apertures 39a of the tongue 39 may be aligned with one of the positioning holes 74 of the locator 36 and thereafter one of the pins 75 may be positioned in the locating aperture 39a and the positioning hole 74 thereby securing the slider 26 to the locator 36.

From the above discussion, it should be appreciated that the locking pins 23 (see FIG. 3) and the locking holes 25 (see FIG. 4) cooperate to lock or otherwise position the base 24 within any one of a number of various positions relative to the slider 26, whereas the locating apertures 39a (see FIG. 5) and the positioning holes 74 (see FIG. 6) cooperate in order to lock or otherwise position the slider 26 within any one of a number of various positions relative to the locator 36. This allows the cannula retainer 12 to be adjusted in order to accommodate various levels of surface tension associated with the outer surface 18a of the body 18. More specifically, surface tension on the outer surface 18a of the body 18 is dependent on the amount of fat, subcutaneous tissue, and/or intra-abdominal pressure which is present within the body 18. As the amount of fat, subcutaneous tissue, and/or intra-abdominal pressure present in the body 18 is increased, the surface tension associated with the outer surface 18a of the body 18 is decreased thereby requiring the angle of insertion of the cannula 16 to be altered. It should be appreciated that a relatively low surface tension associated with the outer surface 18a of the body 18 may require the angle of insertion of the cannula 16 to be altered a number of times in order to access the desired anatomical structure within the body 18. The cooperation of (1) the locking pins 23 and the locking holes 25, and (2) the locating apertures 39a and the positioning holes 74, respectively, allow the surgeon to adjust (1) the position of the base 24 and hence the enclosed structure 22 relative to the slider 26, and (2) the position of the slider 26 relative to the locator 36, respectively, thereby adjusting the angle of insertion of the cannula 16 in order to account for variations in surface tension of the outer surface 18a of the body 18. Hence, the surgeon may more readily access the desired anatomical structure within the body 18.

As described above, the cannula retainer 12 secures the portion 44 of the cannula 16 to the body 18. Secured to a top portion 78 of the cannula 16 (see FIG. 1) is the instrument retainer 14. The instrument retainer 14 includes a left retainer portion 28, a right retainer portion 30, and a ball-shaped instrument holder 32 as shown in FIG. 1. The left retainer portion 28 and the right retainer portion 30 are non-movably secured to the top portion 78 of the cannula 16. Collectively, the left retainer portion 28 and the right retainer portion 30 are referred to as a "retainer body". The ball-shaped instrument holder 32 is movably secured to the left retainer portion 28 and the right retainer portion 30.

Figure 10:
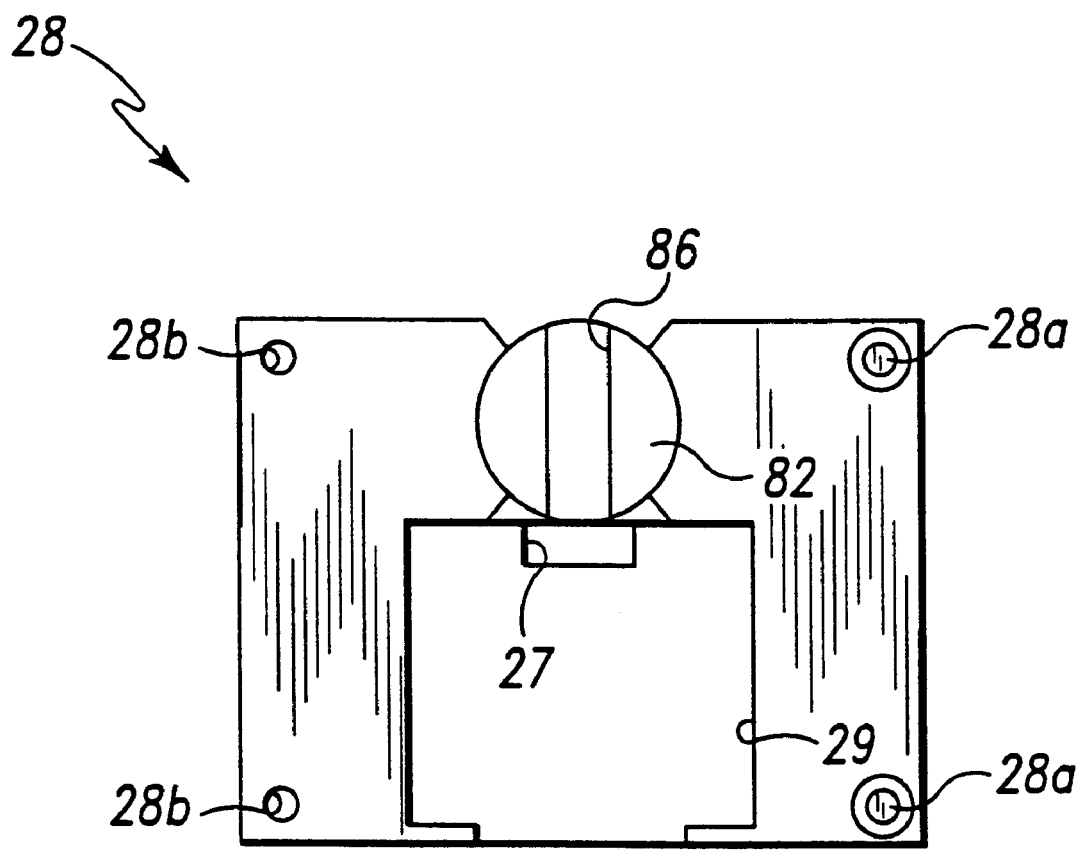
FIG. 10 is a side elevational view of the left retainer portion of the instrument retainer of the cannula and instrument retaining assembly of FIG. 1 (Note: the brake assemblies 92, 94 have been removed for clarity of description)
Figure 11:
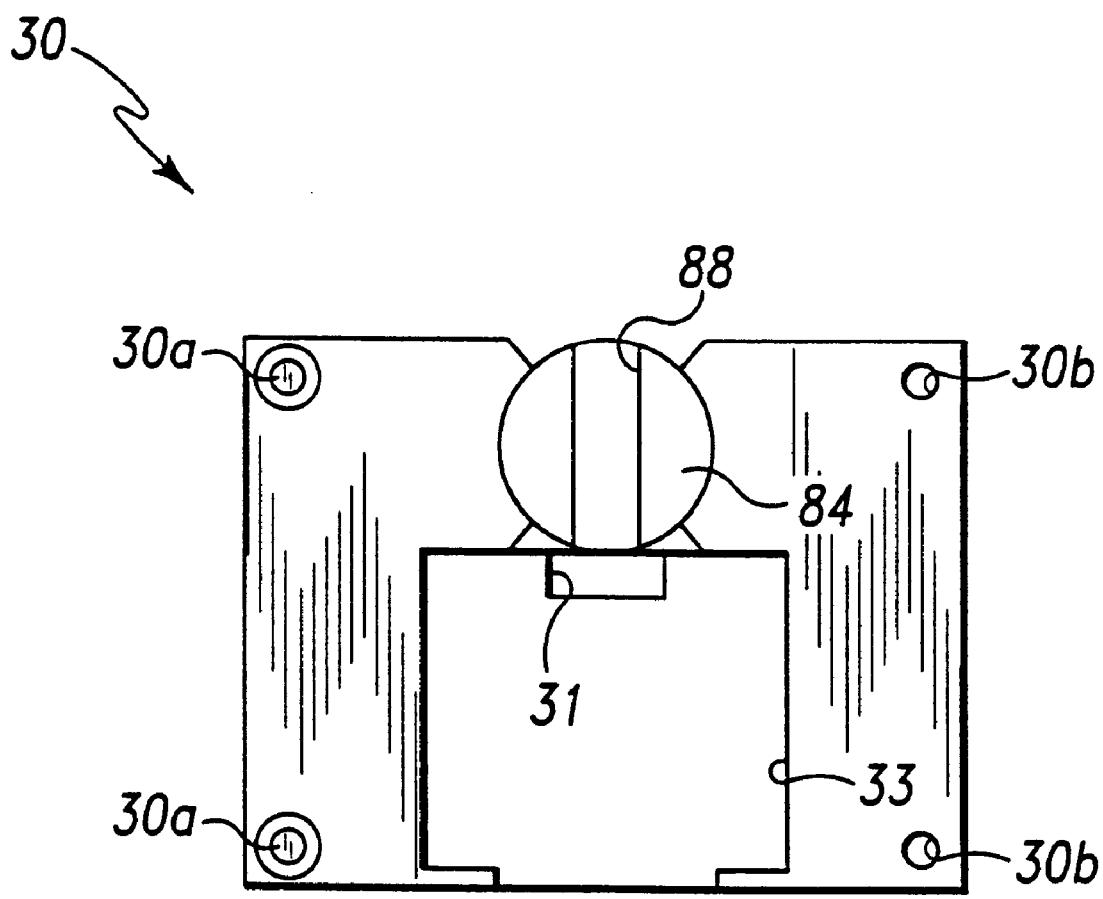
FIG. 11 is a side elevational view of the right retainer portion of the instrument retainer of the instrument retainer of the cannula and instrument retaining assembly of FIG. 1 (Note: the brake assemblies 92, 94 have been removed for clarity of description)

As shown in FIGS. 10–11, the left retainer portion 28 has a number of posts 28a and a number of apertures 28b defined, whereas the right retainer portion 30 has a number of posts 30a and apertures 30b defined therein. In order to secure the left retainer portion 28 to the right retainer portion 30, the posts 28a are received into the apertures 30b and the posts 30a are received into the apertures 28b. It should be appreciated that the posts 28a, 30a may be secured within the apertures 28b, 30b in any acceptable manner. For example, the posts 28a, 30a may be snap-fit or friction-fit within the apertures 28b, 30b.

The left retainer portion 28 has a cavity 27 and a cavity 29 defined therein. The cavity 27 and the cavity 29 cooperate in order to receive the upper portion 78 of the cannula 16. Note that a first flange of a pair of flanges 78a of the upper portion 78 of the cannula 16 (see FIG. 1) is received into the cavity 27.

Similarly, the right retainer portion 30 has a cavity 31 and a cavity 33 defined therein. The cavity 31 and the cavity 33 cooperate in order to receive the upper portion 78 of the cannula 16. Note that a second flange of the pair of flanges 78a of the upper portion 78 of the cannula 16 (see FIG. 1) is received into the cavity 31.

As shown in FIGS. 1 and 10–11, the ball-shaped instrument holder 32 includes a left holder portion 82 and a right holder portion 84. The left holder portion 82 has a channel 86 defined therein, whereas the right holder portion 84 has a channel 88 defined therein. The channel 86 and the channel 88 cooperate to define a passageway in which the medical instrument 20 is secured as shown in FIG. 1. The medical instrument 20 extends through the passageway defined by the channel 86 and the channel 88 and thereafter extends through a lumen 90 defined in the cannula 16 in order to access the body 18.

The ball-shaped instrument holder 32, and hence the medical instrument 20 secured therein, may rotate relative the left retainer portion 28 and the right retainer portion 30 thereby permitting the surgeon to alter the angle and position of the medical instrument. The instrument retainer 14 includes a left brake assembly 92 and a right brake assembly 94 as shown in FIG. 1. The left brake assembly 92 includes a brake member 96. The brake member 96 includes a handle portion 96a and a brake portion 96b. The brake member 96 is pivotally attached to the left retainer portion 28 via a pin joint 98 as shown in FIG. 1. Similarly, the right brake assembly 94 includes a brake member 100. The brake member 100 includes a handle portion 100a and a brake portion 100b. The brake member 100 is pivotally attached to the right retainer portion 30 via a pin joint 102.

The brake members 96 and 100 are positionable between a brake position and a release position. In order to position the brake members 96 and 100 in the brake position or otherwise prevent the ball-shaped instrument holder 32 from moving relative to the left retainer portion 28 and the right retainer portion 30, the brake members 96 and 100 are pivoted relative to the pin joints 98 and 102, respectively. More specifically, when the handle portion 96a of the brake member 96 is urged in the general direction of arrow D of FIG. 1, the brake portion 96b of the brake member 96 is urged in the general direction of arrow E of FIG. 1 and thereby is urged into contact with the left holder portion 82 of the ball-shaped instrument holder 32. Moreover, when the handle portion 100a of the brake member 100 is urged in the general direction of arrow E of FIG. 1, the brake portion 100b of the brake member 100 is urged in the general direction of arrow D of FIG. 1 and thereby is urged into contact with the right holder portion 84 of the ball-shaped instrument holder 32. It should be appreciated that when the brake portions 96b and 100b are in contact with the left holder portion 82 and the right holder portion 84, the ball-shaped instrument holder 32 is prevented from moving relative the left retainer portion 28 and the right retainer portion 30.

In order to position the brake members 96 and 100 in the release position or otherwise allow the ball-shaped instrument holder 32 to move relative to the left retainer portion 28 and the right retainer portion 30, the brake members 96 and 100 are pivoted relative to the pin joints 98 and 102, respectively. More specifically, when the handle portion 96a of the brake member 96 is urged in the general direction of arrow E of FIG. 1, the brake portion 96b of the brake member 96 is urged in the general direction of arrow D of FIG. 1 and thereby is spaced apart from the left holder portion 82 of the ball-shaped instrument holder 32. Moreover, when the handle portion 100a of the brake member 100 is urged in the general direction of arrow D of FIG. 1, the brake portion 100b of the brake member 100 is urged in the general direction of arrow E of FIG. 1 and thereby is spaced apart from the right holder portion 84 of the ball-shaped instrument holder 32. It should be appreciated that when the brake portions 96b and 100b are spaced apart from the left holder portion 82 and the right holder portion 84, respectively, the ball-shaped instrument holder 32 is permitted to move relative the left retainer portion 28 and the right retainer portion 30.

Figure 12:
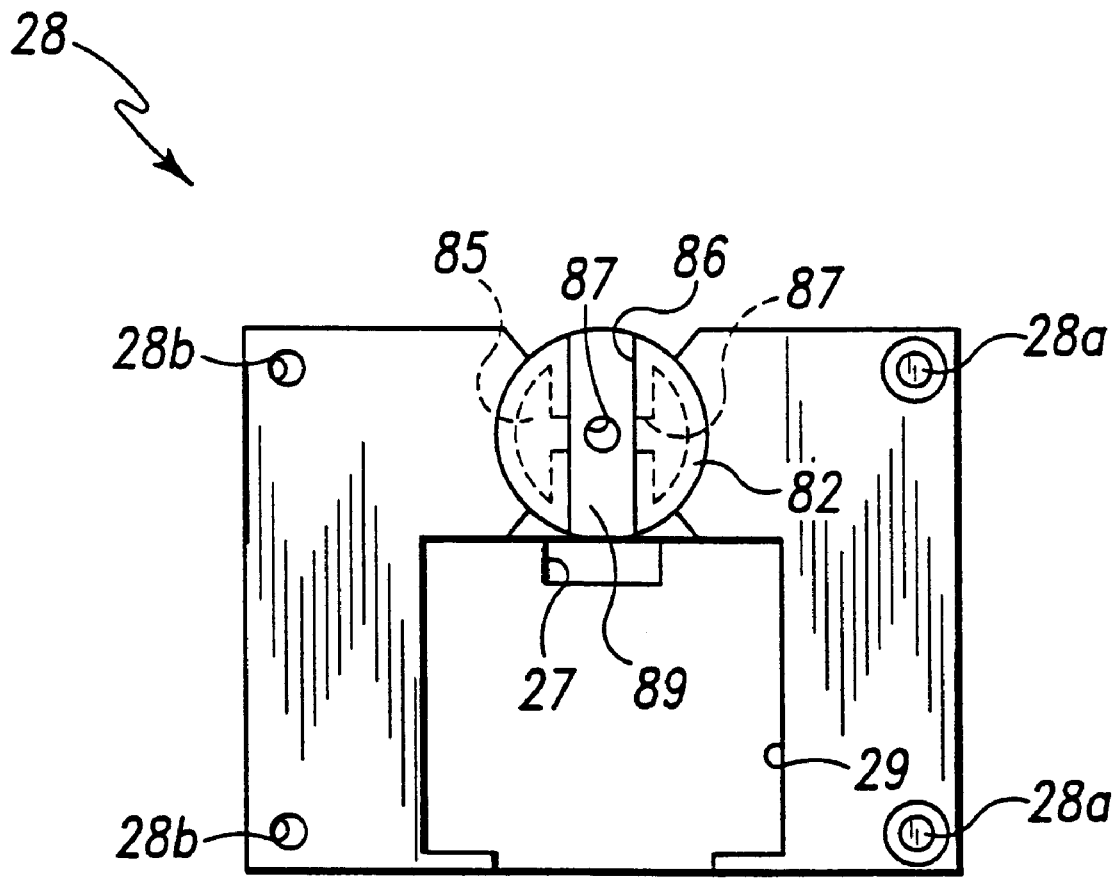
FIG. 12 is a side elevational view of a second embodiment of the left retainer portion of the instrument retainer which incorporates the features of the present invention therein (Note: the brake assemblies 92, 94 have been removed for clarity of description)
Figure 13:
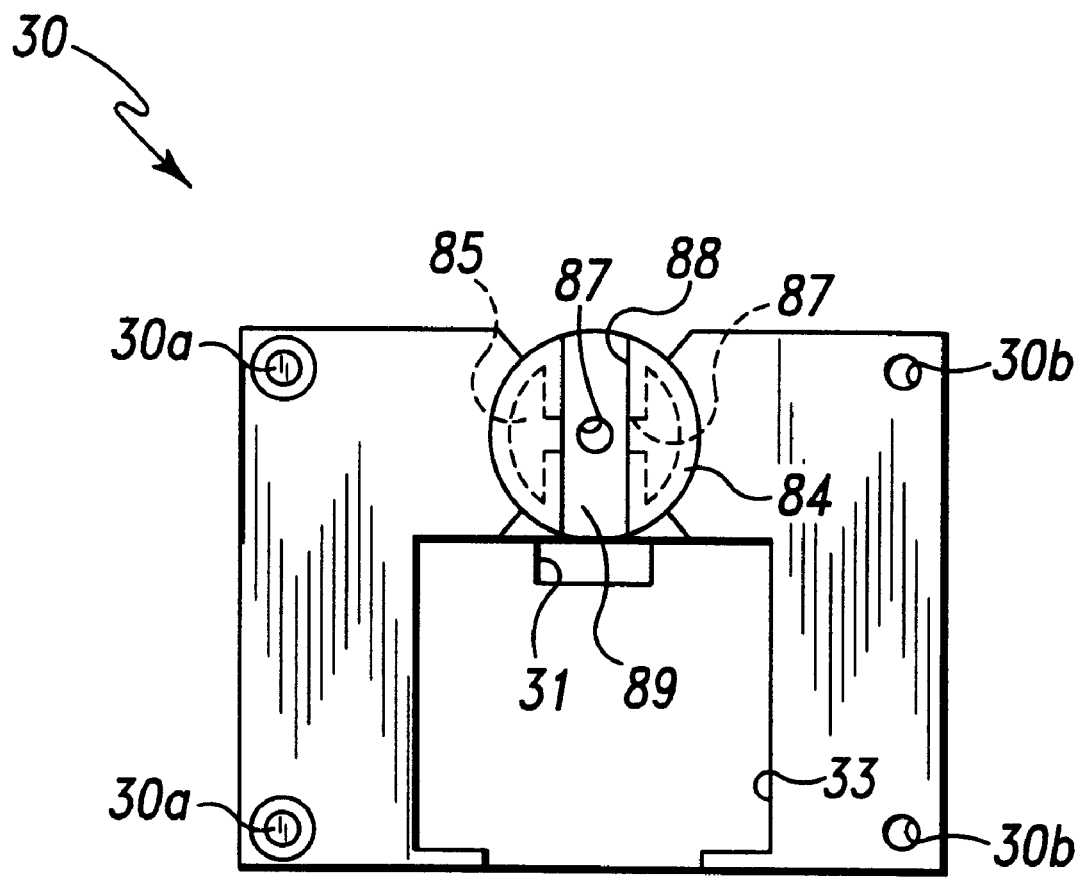
FIG. 13 is a side elevational view of a second embodiment of the right retainer portion of the instrument retainer which incorporates the features of the present invention therein (Note: the brake assemblies 92, 94 have been removed for clarity of description).

The ball-shaped instrument holder 32 may also be configured to apply a biologically active compound to an outer surface of the instrument 20 as the instrument 20 is received into the passageway defined by the channels 86, 88. Such biologically active compounds may include an antibiotic or a cytotoxic agent. In particular, the left holder portion 82 and the right holder portion 84 may both include a fluid reservoir 85 as shown in FIGS. 12–13. In addition, the left holder portion 82 and the right holder portion 84 may both include a number of fluid holes 87 defined in a sidewall 89. The fluid holes 87 are provided to place the fluid reservoir 85 into fluid communication with the passageway defined by the channels 86, 88 thereby allowing a fluid such as the biologically active compound to be advanced from the fluid reservoir 85 and into contact with the medical instrument 20 within the passageway defined by the channels 86, 88.

A large number of antimicrobial agents (antibiotics) or antiseptics are contemplated for use as the biologically active compound in the present invention. Preferably, where possible, the antibiotic should be active against both Gram-positive and Gram-negative pathogens. The following are illustrative of the antibiotics and/or antiseptics which can be contained in the fluid reservoir 85 to aid in the control, inhibition or prevention of infections: (i) metal salts, or like compounds with antibacterial metal ions, e.g. copper or silver, and optionally with additional nonmetallic ions of antibacterial properties; (ii) typical antibiotics, e.g. neomycin, soframycin, bacitracin, polymcin; (iii) antibacterials such as chlorhexidine and its salts; (iv) quaternary ammonium compounds, e.g. centrimide, domiphen bromide, and polymeric quaternaries; (v) iodophors such as povidone iodine, and polyvinylpyrrolidone-iodine (PVP-l); (vi) acridine compounds such as 9-aminoacridine, 3,6-diaminoacridine and 6,9-diamino-2-ethoxyacridine; and (vii) biguanidine compounds such as 1,6-di(4-chlorophenylbiguanido)hexane, diaminohexylbiguanide, 1,6-di(aminohexylbiguanido)hexane, and polyhexamethylenebiguanide. Additional suitable antibiotics include aminoglycoside antibiotics such as amikacin, butirosin, dideoxykanamycin B (DKP), fortimycin, gentamycin, kanamycin, lividomycin, neomycin, netilmicin, ribostamycin, sagamycins, seldomycins and their epimers, sisomicin, sorbistin, tobramycin, streptomycins, linkomycins such as clindamycin, lincomycin and rifamycins such as rifampicin and rifamycin. Antibiotics such as polymyxin B sulfate-neomycin sulfate, cleocin phosphate ® (available from the Upjohn Company, Kalamazoo, Mich.) and erythromycin ethylsuccinate are also contemplated.

Examples of suitable antiseptics include bromchlorophen, hexetidine, buclosamide, salicylic acid, cerium nitrate, chlorhexidine, 5-chloro-8-hydroxyquinoline, copper 8-hydroxyquinolate, acridine orange, undecenoic acid, undecoylium chloride and silver salts such as silver sulfadiazine, mafenide, nitrofurazole, cloflucarban, tribromasalan, taurolin and noxythiolin.

Tumor cell destroying compounds, hereinafter referred to as cytotoxic compounds, can also be contained in the fluid reservoir 85. These compounds include cisplatin, carboplatin, 5-fluorouracil, providoneiodine, tumor necrosis factor (TNF)-α, tauromustine, mitomycin C, camptothecin, bleomycin, indomethacin, N-methyl formamide, tamoxifen, sodiumhypochlorite, chlorhexidinecetrimide, adriamycin, methotrexate. Tumor cell destroying compounds also include antimetabolites such as cytarabine, azaribine, mercaptopurine, thioguanine, tomudex, multi-targeted antifol, capecitabine; natural products such as vinblastine, vincristine, dactinomycin, daunorubicin, doxorubicin, bleomycin, mithramycin, mitomycin; and other miscellaneous agents such as cisplatin, hydroxyurea, procarbazine and mitotane, Alkylating agents such as mechlorethamine, nitrogen mustards, ethlenimine derivatives, alkyl sulfonates, nitrosoureas, and triazenes are also contemplated. Moreover, the compounds disclosed by Krakoff, Irwin H. in *Systemic Treatment of Cancer,* CA Cancer J. Clin., vol. 46, No. 3, pages 134–141 (May/June 1996), which is incorporated herein by reference, are contemplated for being contained in the fluid reservoir 85.

In addition antiangiogenesis agents such as angiostatin are included in the group of cytotoxic compounds to be contained in the fluid reservoir 85. Moreover, antibodies, including human monoclonal antibodies are included as cytotoxic compounds. Preferably, the human monoclonal antibody HuMab SK1 as described by Chang, Helena R. et al. in *Human Monoclonal Antibody SK1-Mediated Cytotoxicity Against Colon Cancer Cells,* Dis. Colon Rectum, vol. 36, No. 12, pages 1152–1157 (December 1993) which is incorporated herein by reference, may be contained in the fluid reservoir 85. Other monoclonal antibodies may also be contained in the fluid reservoir 85, for example those produced from hybridomas having the accession numbers HB8573, HB8232 and HB8250 available from the American Type Culture Collection, located at 12301 Parklawn Drive, Rockville Md., 20852. Furthermore, interleukin 2 (IL-2), cytokines or lymphokines are also included in the group of cytotoxic compounds of the present invention. It should also be understood that a combination of any of the above compounds may be contained in the fluid reservoir 85.

If necessary, in order to keep the biologically active compound from falling or sliding off of the medical instrument 20 due to gravity as it is being advanced through the lumen 90, the biologically active compound may contain a suitable pharmaceutically acceptable carrier. A pharmaceutically acceptable carrier will also aid in retaining all, or a portion of, the biologically active compound on the outer surface of the medical instrument 20 as it is being advanced through an opening in the body 18. Such pharmaceutically acceptable carriers include known excipients and auxiliaries which facilitate the processing of the biologically active compound into a preparation which has the appropriate consistency to be disposed on the outer surface of the medical instrument 20.

Suitable excipients which may be used to prepare a pharmaceutically acceptable carrier, such as a viscous solution, include fillers such as saccharides, for example lactose or sucrose, mannitol or sorbitol, cellulose preparations (e.g. carboxymethyl cellulose) and/or calcium phosphates, for example tricalcium phosphate or calcium hydrogen phosphate. If desired, disintegrating agents may be added such as carboxymethyl-starch, cross-linked polyvinyl pyrrolidone, agar, or alginic acid or a salt thereof, such as sodium alginate. Additionally, silica, talc, stearic acid or salts thereof such as magnesium stearate or calcium stearate, and/or polyethylene glycol can be used.

In addition, a suspension of the biologically active compound may be contained within the reservoir 85. Suitable vehicles for such suspensions include sesame oil or synthetic fatty acid esters, for example, ethyl oleate or triglycerides. Such suspensions can include substances which increase the viscosity of the suspension including, for example, sodium carboxymethyl cellulose, sorbitol and/or a dextran.

The exact formulation of a pharmaceutically acceptable carrier will depend upon the particular nature of the biologically active compound to be contained in the fluid reservoir 85. Moreover, the concentration and amount of the biologically active compound to be disposed on the medical instrument 20 will depend upon the age, sex, weight, condition of the recipient, kind of concurrent treatment, if any, frequency of treatment and the nature of the effect desired. However, the amount of the biologically active compound to be dispose on the medical instrument 20 is large enough to produce the desired effect but not so large as to cause adverse side effects, such as unwanted cross reactions, anaphylactic reactions and the like. Counterindication, if any, immune tolerance and other variables will also affect the proper amount to be disposed on the medical instrument 20. The exact formulation of a pharmaceutically acceptable carrier and the amount of the biologically active compound contained therein (and therefore the amount disposed on the medical instrument) is easily determinable by one of ordinary skill in the art from only routine experimentation and by applying well know principles of therapeutics as set forth, for example, in Gilman, Alfred G. et al., eds., *The Pharmacological Basis of Therapeutics,* 6th Edition, Macmillan Publishing Co., Inc. New York, N.Y. (1980) which is herein incorporated by reference. Preferably, such preparations will contain about 0.001 to about 99 percent the biologically active compound together with the pharmaceutically acceptable carrier.

For example, the biologically active compound is suspended or dissolved in a 1% aqueous (weight/volume) solution of carboxymethyl cellulose (CMC) before being applied to the medical instrument 20 (prospective example). Such a CMC solution provides the necessary viscosity to keep the biologically active compound from sliding or rolling off the medical instrument 20 when it is being advanced through the lumen 90 and into an opening in the body 18.

In operation, the locator 36 may first be sutured to the outer surface 18a of the body 18 via the suture holes 76 (see FIG. 6). The base 24 may then be rotatably secured to the slider 26 by snapping the attaching plug 66 into the attaching aperture 67. Thereafter, the tongues 39 of the slider 26 are received into the grooves 72 of the locator 36 thereby slidably securing the slider 26 and hence the base 24 to the locator 36. It should be appreciated that for convenience reasons the base 24 may be secured to the slider 26, and the slider 26 may be secured to the locator 36 prior to use thereof by the surgeon.

Thereafter, the cannula 16, along with the other components associated with a trocar assembly such as a trocar or obturator (not shown), are positioned within the opening of the cannula retaining ring 21 and the access opening 42. After which, the cannula 16 is inserted into the body 18 in a known manner.

The surgeon may then (1) slide and secure the slider 26 relative to the locator 36 via use of the pins 75 within the locating apertures 39a and the positioning holes 74, and/or (2) rotate and secure the base 24 relative to the slider 26 via use of the locking pins 23 and the locking holes 25 in order to position the cannula 16 in a desired angle and position. The surgeon may also move the cannula 16 upwardly and downwardly via use of the cannula retaining ring 21. Once the surgeon has positioned the cannula 16 in the desired position, the fluid port 34 may be placed in fluid communication with the vacuum source V thereby placing the bag 40 of the enclosed structure 22 in its evacuated mode of operation in which the cannula 16 is prevented from moving relative to the enclosed structure 22.

Once the portion 44 of the cannula 16 is secured to the cannula retainer 12 as described above, the medical instrument 20 may be advanced through the lumen 90 of the cannula 16 (see FIG. 1) and thereafter the instrument retainer 14 may then be secured to the upper portion 78 of the cannula 16. More specifically, the left retainer portion 28 and the right retainer portion 30 are connected together via the posts 28a, 30a and the apertures 28b, 30b in the manner previously described thereby securing the medical instrument 20 within the passageway defined by the channel 86 of the left holder portion 82 and the channel 88 of the right holder portion 84. It should be noted that as the medical instrument 20 is advanced through the passageway defined by the channels 86, 88, the biologically active compound may be applied to the outer surface thereof in the manner previously described. Hence, the medical instrument 20 may be moved upwardly and downwardly relative to the ball-shaped instrument holder 32 to apply the biologically active compound to the outside surface thereof at various times throughout a given surgical procedure.

Thereafter, the surgeon may alter the angle and position of the medical instrument 20 by rotating the ball-shaped instrument holder 32. Once the surgeon positions the medical instrument 20 in a desired angle and position, the ball-shaped instrument retainer 32 may be braked by the brake assemblies 92 and 94 in the manner previously described.

Alternatively, the cannula 16 may be first inserted into the body 18 prior to attachment thereto of the cannula and instrument retainer assembly 10. In this case, prior to suturing the locator 36 to the outer surface 18a of the body 18, the attaching plug 66 is snapped into the attaching aperture 67 thereby rotatably securing the base 24 to the slider 26. In addition, the tongues 39 of the slider are received into the grooves 72 of the locator 36 thereby slidably securing the slider 26 and hence the enclosed structure 22 to the locator 36. The cannula 16 may then be slidably received into the open end of the channel 37 of the slider 26 (see FIG. 4), the channel 35 of the locator 36 (see FIG. 6) and the open end of the elongated channel 43 of the enclosed structure 22 (see FIG. 2). Thereafter, the cannula 16 may be slid into the opening 21a of the cannula retaining ring 21 and the access opening 42. After which, the locator 36 may be sutured to the outer surface 18a of the body cavity via suture holes 76. It should be appreciated that for convenience reasons the base 24 may be secured to the slider 26, and the slider 26 may be secured to the locator 36 prior to use thereof by the surgeon.

The surgeon may then (1) slide and secure the slider 26 relative to the locator 36 via use of the pins 75 within the locating apertures 39a and the positioning holes 74, and/or (2) rotate and secure the base 24 relative to the slider 26 via use of the locking pins 23 and the locking holes 25 in order to position the cannula 16 in a desired angle and position. The surgeon may also move the cannula 16 upwardly and downwardly via use of the cannula retaining ring 21. Once the surgeon has positioned the cannula 16 in the desired position, the fluid port 34 may be placed in fluid communication with the vacuum source V thereby placing the bag 40 of the enclosed structure 22 in its evacuated mode of operation in which the cannula 16 is prevented from moving relative to the enclosed structure 22.

Once the portion 44 of the cannula 16 is secured to the cannula retainer 12 as described above, the medical instrument 20 may be advanced through the lumen 90 of the cannula 16 (see FIG. 1) and thereafter the instrument retainer 14 may then be secured to the upper portion 78 of the cannula 16. More specifically, the left retainer portion 28 and the right retainer portion 30 are connected together via the posts 28a, 30a and the apertures 28b, 30b in the manner previously described thereby securing the medical instrument 20 within the passageway defined by the channel 86 of the left holder portion 82 and the channel 88 of the right holder portion 84. It should be noted that as the medical instrument 20 is advanced through the passageway defined by the channels 86, 88, the biologically active compound may be applied to the outer surface thereof in the manner previously described. Hence, the medical instrument 20 may be moved upwardly and downwardly relative to the ball-shaped instrument holder 32 to apply the biologically active compound to the outside surface thereof at various times throughout a given surgical procedure.

Thereafter, the surgeon may alter the angle and position of the medical instrument 20 by rotating the ball-shaped instrument holder 32. Once the surgeon positions the medical instrument 20 in a desired angle and position, the ball-shaped instrument retainer 32 may be braked by the brake assemblies 92 and 94 in the manner previously described.

From the previous discussion, it should be appreciated that the cannula 16 may be positioned in a number of predetermined positions along three axes (e.g. the x-, y-, and z-axis) by use of the cannula retainer 12. In particular, the cannula 16 may be positioned along the x-axis by sliding the slider 26 relative to the locator 36, whereas the cannula 16 may be positioned along the y-axis by rotating the base 24 relative to the slider 26. In addition, the cannula 16 may be positioned along the z-axis by moving the cannula 16 relative to the cannula retaining ring 21.

Similarly, it should be appreciated that the medical instrument 20 may be positioned in a number of predetermined positions along three axes (e.g. the x-, y-, and z-axis) by use of the instrument retainer 14. In particular, the medical instrument 20 may be positioned along the x-axis and the y-axis by rotating the ball-shaped instrument holder 32. In addition, the medical instrument 20 may be positioned along the z-axis by sliding the medical instrument 20 relative to the passageway defined in the ball-shaped instrument holder 32. Moreover, the medical instrument 20 may be positioned in a number of predetermined positions relative the retainer body via 360° rotation of the ball-shaped instrument holder 32.

While the invention has been illustrated and described in detail in the drawings and foregoing description, such illustration and description is to be considered as exemplary and not restrictive in character, it being understood that only the preferred embodiments have been shown and described and that all changes and modifications that come within the spirit of the invention are desired to be protected.

It should be appreciated that the cannula and instrument retaining assembly 10 may serve as a platform from which additional technology may be utilized in conjunction with minimally invasive surgery. For example, the cannula and instrument retaining assembly 10 may form a base upon which a number of electronic devices may be used in remote access minimally invasive surgery and robotic minimally invasive surgery. Such electronic devices may include microprocessors, infrared receptors and sensors, and pressure sensors which may be used to facilitate the advancement of minimally invasive surgery (e.g. remote access minimally invasive surgery and robotic minimally invasive surgery).

In addition, although the cannula retainer 12 has been described as a device for holding the cannula 16 of a trocar assembly, it should be appreciated that the present invention may be used for numerous industrial purposes such as positioning and stabilizing a work tool. For example, the present invention may be used to position and stabilize a drill bit or a telescope. Moreover, the present invention is relatively resistant to pressure changes relative to atmospheric pressure thereby facilitating its use in environments subjected to varying pressures such as space or underwater exploration.

What is claimed is:

1. A method for securing a medical instrument to a cannula of a trocar assembly, wherein said cannula defines a cannula passageway extending therethrough, comprising the steps of:

attaching an instrument retainer to said cannula, said instrument retainer including an instrument holder (1) having a passageway extending therethrough and (2) being rotatable secured to said instrument retainer, inserting said instrument through said passageway, and rotating said instrument holder relative to said instrument retainer so that said passageway of said instrument holder tilts relative to said cannula passageway.

2. The method of claim 1, wherein said inserting step includes the step of securing said instrument within said passageway of said instrument holder.

3. The method of claim 1, wherein (1) said instrument holder includes a ball-shaped member having said passageway extending therethrough, and (2) said instrument retainer further includes a brake, further comprising the step of:

positioning said brake in contact with said ball-shaped member so as to prevent rotation of said ball-shaped member.

4. The method of claim 3, further comprising the step of:

spacing said brake apart from said ball-shaped member so as to enable rotation of said ball-shaped member.

5. The method of claim 1, wherein:

said instrument retainer further includes (1) a first retainer portion having a post secured thereto, and (2) a second retainer portion having an aperture defined therein, and said attaching step includes the step of moving said post relative to said aperture so that said post is received into said aperture.

6. The method of claim 5, wherein:

said cannula includes a first flange secured thereto, said first retainer portion further has a first cavity defined therein, and said attaching step includes the step of advancing said first flange into said first cavity of said first retainer portion.

7. The method of claim 6, wherein:

said cannula includes a second flange secured thereto, said second retainer portion further has a second cavity defined therein, and said attaching step further includes the step of advancing said second flange into said second cavity of said second retainer portion.

8. The method of claim 1, wherein said instrument holder has (1) a fluid reservoir defined therein, and (2) a sidewall having a fluid hole defined therein, further comprising the steps of:

positioning a fluid within said fluid reservoir; and advancing said fluid through said fluid hole so that said fluid contacts said instrument within said passageway of said instrument holder.

* * * * *